United States Patent [19]

Tebbe

[11] Patent Number: 5,734,590

[45] Date of Patent: Mar. 31, 1998

[54] RECORDING MEDIUM AND DEVICE FOR GENERATING SOUNDS AND/OR PICTURES

[76] Inventor: Gerold Tebbe, 11, Avenue Princesse Grace, MC-9800 Monaco, Monaco

[21] Appl. No.: 416,854

[22] PCT Filed: Oct. 16, 1993

[86] PCT No.: PCT/EP93/02858

§ 371 Date: Apr. 14, 1995

§ 102(e) Date: Apr. 14, 1995

[87] PCT Pub. No.: WO94/09493

PCT Pub. Date: Apr. 28, 1994

[30] Foreign Application Priority Data

Oct. 16, 1992 [DE] Germany ............ 42 34 926.5
Feb. 19, 1993 [DE] Germany ............ 43 05 141.3
Apr. 22, 1993 [DE] Germany ............ 43 13 119.0

[51] Int. Cl.$^6$ ............................................. G06F 17/00
[52] U.S. Cl. ............................................. 364/514 A
[58] Field of Search ............... 364/514 A, 514 R, 364/578, DIG. 1, DIG. 2; 345/156; 84/645, 670, 464 R, 601, 602, 609, 611, 634, 635, 641, 642, DIG. 1, DIG. 2, DIG. 29

[56] References Cited

U.S. PATENT DOCUMENTS

| | | | |
|---|---|---|---|
| 4,315,502 | 2/1982 | Gorges | 434/236 |
| 4,629,604 | 12/1986 | Spector | 422/124 |
| 4,753,148 | 6/1988 | Johnson | 84/464 R |
| 4,952,024 | 8/1990 | Gale | 348/53 |
| 4,988,557 | 1/1991 | Charbonneau | 428/208 |
| 5,062,097 | 10/1991 | Kumaoka | 358/335 |
| 5,113,738 | 5/1992 | Krucoff | 360/27 |
| 5,513,129 | 4/1996 | Bolas et al. | 364/578 |

FOREIGN PATENT DOCUMENTS

| | | |
|---|---|---|
| 0 076 125 | 4/1983 | European Pat. Off. . |
| 0 359 325 | 3/1990 | European Pat. Off. . |
| 0 508 939 | 10/1992 | European Pat. Off. . |
| 2 670 568 | 6/1992 | France . |
| 1566652 | 1/1971 | Germany . |
| 40 03 476 | 8/1991 | Germany . |
| 40 03 477 | 8/1991 | Germany . |
| 40 33 076 | 4/1992 | Germany . |
| 4033076 | 2/1993 | Germany . |
| 55-0025276 | 2/1980 | Japan . |
| 2007969 | 1/1990 | Japan . |
| 4022369 | 1/1992 | Japan . |
| 1 270 052 | 4/1972 | United Kingdom . |

OTHER PUBLICATIONS

"Decoder IC for an Automatic Video Program Identification System (VPS)", *IEEE Transactions on Consumer Electronics*, vol. CE-32, No. 3, Aug., 1986.

Patent Abstracts of Japan, vol. 16, No. 257 (C-0949), Jun. 11, 1992 (JP,A,04 058 956, Feb. 25, 1992).

Patent Abstracts of Japan, vol. 15, No. 317 (C-0858), Aug. 13, 1991 (JP,A,03 121 074, May 23, 1991).

Patent Abstracts of Japan, vol. 14, No. 134 (C-0701), Mar. 14, 1990 (JP,A,02 007 969, Jan. 11, 1990).

(List continued on next page.)

*Primary Examiner*—Alpus H. Hsu
*Assistant Examiner*—Seema S. Rao
*Attorney, Agent, or Firm*—Lowe, Price, LeBlanc & Becker

[57] ABSTRACT

A device is provided for generating sounds and/or pictures together with additional and correlated fragrance release for a more complete stimulation of the senses of an audience. The device includes a stimulus generator control providing signals having a low rate of change and a digital control signal memory addressed by a control unit which activates the control signal memory during a read-out operation by an addressing counter and during a reading-in operation in dependence on incoming control signals from a received utility signal source, e.g., a radio or television broadcast.

30 Claims, 14 Drawing Sheets

OTHER PUBLICATIONS

Patent Abstracts of Japan, vol. 10, No. 197 (E–148), Jul. 10, 1986 (JP,A,61 041 229, Feb. 27, 1986).

Patent Abstracts of Japan, vol. 16, No. 180 (C–0935), Apr. 30, 1992 (JP,A,04 022 369, Jan. 27, 1992).

Patent Abstracts of Japan, vol. 4, No. 56 (E–008), Apr. 25, 1980 (JP,A,55 025 276, Feb. 22, 1980).

Database WPI, Section EI, Week 8429, Derwent Publications, Ltd., London, Great Britain, Class S06, An 84–177169 (AU–D–2 144 283).

Patent Abstracts of Japan, vol. 15, No. 401 (E–1121), Oct. 11, 1991 (JP,A,03 163 796, Jul. 15, 1991).

Patent Abstracts of Japan, vol. 15, No. 401 (E–1121), Oct. 11, 1991 (JP,A,03 163 797, Jul. 15, 1991).

Patent Abstracts of Japan, vol. 17, No. 471 (P–1601), Aug. 26, 1993 (JP,A,05 109 253, Apr. 30, 1993).

RECORDING MEDIUM AND DEVICE FOR GENERATING SOUNDS AND/OR PICTURES

FIELD OF THE INVENTION

The invention relates to a recording medium and to a device for generating sounds and/or pictures, and more particularly to a recording medium which provides with sight and sound additional sensory experience including correlated fragrances.

BACKGROUND OF THE RELATED ART

Conventional recording media and devices for generating sounds or pictures generate relatively rapidly varying acoustic and/or visual stimuli. The rapid variations of the stimuli correspond to man's high information absorption capacity on average, and for works of classical music, spoken works and the reproduction of theatre performances or the reproduction of films are largely fixed as directed by the author or artist.

When audio or video recordings are to be played back by a listener or viewer for his own interest at home for recreation purposes, absolute fidelity to the work is not always what matters. According to the invention, it is possible to obtain for that application an additional relaxing or, alternatively, stimulating effect by providing in the device generating the sounds and/or pictures and on a recording medium, in addition, a source of control signals which provides control signals that preferably vary only slowly in comparison with the acoustic and/or visual stimuli and by which an additional stimulus generator can be actuated. That additional stimulus generator may generate visual, tactile or sensory stimuli or may be a further acoustic or visual stimulus generator. By means of the additional, slowly varying stimuli, a relaxing and calming or, alternatively, a stimulating effect is produced on the listener or viewer, depending upon the kind of stimulus generator used.

Advantageous developments of the invention are specified in subclaims.

The development of the invention according to claim 2 is advantageous with regard to disentangling audio and/or video signals, on the one hand, and control signals, on the other hand, using technically simple means.

If the recording medium is constructed in accordance with claim 3, no additional pick-up head is required in the playback device in order to read out the control signals. The control signals for the further stimulus generators are read in in one package before the audio and/or video signals are read out.

The same advantage is obtained with a recording medium according to claim 4, which has the further advantage that the block of tracks containing the audio and/or video signals remains unchanged as an entirety. This is advantageous both with a view to unlimited playback of the recording medium in a conventional playback device and with a view to using existing master recordings also for the purposes of the invention.

In known media for digitalized audio signals, for example compact discs (CDs) or digital audio tapes (DAT cassettes), a linear resolution of each sampling value of 16 bits is provided. The sampling values are coded in blocks, each data block comprising synchronizing information, a number of sampling values and additional information, for example on the numbering of the individual recordings. The data blocks are combined serially to form a data stream.

For compression of digitalized audio signals, for example to about 3 bits average resolution per sampling value, it is known of the digital audio cassette (DCC) system to split the sampling values spectrally into a number of, for example 16, sub-bands by means of digital filtering and to remove from each sub-band with the aid of psychoacoustic criteria, especially the listening threshold of the human ear owing to the masking properties of masking spectral components, those spectral components which are not audible to the human ear, that is to say which are irrelevant for hearing purposes. Accordingly, this psychoacoustic data compression of audio signals is referred to as sub-band coding with irrelevance reduction. Instead of spectral splitting into sub-bands, it is known of the minidisc (MD) to transform the sampling values by means of a fast Fourier transform from the frequency domain into the time domain and to subject them to irrelevance reduction in groups in the form of time windows. This kind of data compression is referred to as transformation coding with irrelevance reduction.

Both in sub-band coding and in transformation coding, for each sub-band and time window, respectively, the maximum signal level within successive time intervals (corresponding to the length of the successive data blocks) is determined as a scaling factor and is inserted into the relevant data block. The totality of the scaling factors represents the envelope or enveloping curve of the audio signal. Also inserted into each data block is so-called bit allocation information which controls the dequantization of the irrelevance-reduced sampling values in the decoder.

The developments according to claims 5 to 7 are based on the idea of controlling an acoustic, visual and/or scent-producing stimulus generator by means of special control information inserted into that region of each data block of the digital audio medium which is intended for additional information. This control preferably occurs in time- or contents-correlation with the audio signal. A scent-producing stimulus generator consists, for example, of microcapsules containing specific scents. These microcapsules are ruptured, for example by ultrasound signals, in order to release the scents, possibly in metered amounts, the ultrasound signals being generated by an ultrasound generator which is in turn controlled by the recorded control information when it is played back from the recording medium. For example, in keeping with the musical content of the audio signal, additional scent stimuli can be given to the listener as the recording medium is being played, for example in Bruckner's "Mass in A Minor", incense in the middle of the Kyrie and at the beginning of the Sanctus, and the scent of fir trees in the Gloria, thereby making the listening event reproduced resemble the circumstances accompanying the original listening event even more closely. The release of the scents can, as in the example mentioned of the "Mass in A Minor", be limited in time; it is also possible to release scent-neutralising substances purposefully between different scents to avoid mixing of the scents. Besides or instead of scent stimuli, it is also possible with the aid of suitable light generators to supply the listener with visual stimuli in the form of purposefully controlled, changing light effects, as are provided, for example, in discotheques when disco music is being played. Finally, additional acoustic stimuli, for example the rustling of sweet papers or the coughing of the audience in a theatre, can be produced with the aid of noise generators under the control of the recorded control information, in order to make the listening event reproduced especially realistic. In this manner, it is possible to use a digital audio medium or a video medium having digital sound accompaniment to create a multiple sensory experience at virtually no extra cost, thus making its attractiveness to the user considerably greater. An important aspect in that regard is that the recording media according to the invention can be played on conventional playback devices in a compatible manner, the recorded control information not being decoded in that case. The reproduction quality of the digitalized audio signal is fully retained also when the medium according to the invention is played back on conventional playback devices. For a playback device that decodes the recorded control information only slight modification in comparison with the conventional playback device is required inasmuch as the demultiplexer already present in any case in the decoder selects not only the hitherto-customary additional information, such as, for example title of the music in characters or the numbering of the recording, but also the control information further inserted in the data blocks for generating the stimuli. This additionally selected control information either is provided at a separate terminal of the playback device, to which the stimulus generator(s) can be connected by their control inputs, or is converted into an audible or inaudible sound signal which is transmitted to the stimulus generator acoustically in the manner of a remote control.

In accordance with claim 9, the gaps in frequency or time present in radio broadcast signals or television signals can be used for interspersing control signals for actuating stimulus generators.

In accordance with claim 10, edge regions or intermediate regions of pre-recorded recording media for sound and/or pictures can be used for applying stimulus generator control signals.

A playback device of the kind specified in claim 11 differs from a conventional playback device only by the additionally provided control signal memory, a few circuits required for reading data from the control signal memory and, where necessary, a slightly different programming of a central control unit of the device. In its essential parts, the device remains unchanged. A device according to claim 11 can accordingly be manufactured at only small extra cost in comparison with a conventional device.

Using a device according to claim 12, the overall experience obtained by the reproduction of the audio and/or video signals and the additional stimuli can be varied within a wide range and very diversely. In particular, sensory stimuli that can be varied only with a large time constant can be coupled with rather more rapid stimuli which, however, are still slow compared with the audio and/or video playback, for example variations in the brightness of a room, variations in the position of the arms and seat of an armchair and so on.

The development of the invention according to claim 13 ensures that actuation of the further stimulus generators is effected whilst relieving the load on the control unit to a very large extent.

In accordance with claim 15, the advantages of the invention can also be obtained in connection with conventional pre-recorded recording media. Intervention in the playback device is not necessary for this.

It has been found that, by phase-matching of different kinds of stimuli, for example acoustic and visual stimuli, an intensification of the stimulating effect, say the relaxing effect, is achieved. For this purpose, the invention provides a device having the features specified in claim 16.

By means of the development of the invention according to claim 17, that phase coupling can be carried out using very simple equipment, even in existing playback devices. The filter circuit can then either be designed for low frequencies so that the control signal is then derived, for example, from the basic time of the piece of music or the sound of a video recording or, instead, one or more pilot tones can be mixed into the recorded piece and then separated by means of the filter circuit during playback and used to control the stimulus generator.

In accordance with claim 18, the advantages obtained by coupling playback and stimulus generator are also obtained in a piece of music played ad hoc on an electronic musical instrument.

The development of the invention according to claim 19 allows the frequency of the control signal to be set independently of the utility signal, but with phase coupling between the two signals being maintained.

In a device according to claim 20, the control of the stimulus generator which is obtained as a result of coupling to the utility signal can, in addition, be overlaid by a freely varying modulation. Thus, the envelope generator can vary, for example, the amplitude of the control signal in accordance with a sine curve with very low frequency or vary it in accordance with a digital program stored, for example, in a ROM.

In devices for generating sounds and/or pictures hitherto, there was no possibility of sensory stimuli. With a device according to claim 21, an entirely new dimension is created in the reproduction of sound and/or pictures for recreation purposes, which it will also be possible to use in future for multi-stimulation compositions with a specific aim.

A device according to claim 22 is suitable for the simple and effective controlled release of scents in liquid form.

By means of the development of the invention according to claim 23 the release of scents is accompanied by the delivery of additional oxygen.

If microencapsulated scents are used in accordance with claim 24, storage, transport and handling of the scents is especially simple. There is also only little loss of scents if the device is inoperative for a prolonged period. The controllable scent source can be manufactured compactly, in a mechanically simple manner and inexpensively.

This applies especially to a scent source of the kind specified in claim 25 since the rate of scent release can be adjusted in a very simple manner via the angular velocity of the squeezing rollers.

A scent generator of the kind specified in claim 26 is distinguished by especially low operating costs. It also has a construction that is nevertheless simple mechanically and is therefore also suitable as a low-cost mass-produced article.

The development of the invention according to claim 27 ensures that precisely the desired scents are obtained by means of the control signals, since the container block is attached as a unit thereby excluding the possibility of wrong connections.

The development of the invention according to claim 28 is advantageous with regard to obtaining a rapid transport of the scents from the scent generator to the user.

In the case of a scent generator according to claim 29, the user need not trouble with preparation work. The substrates carrying the microencapsulated scents are in the form of ready-for-use products.

The development of the invention according to another variation is advantageous with a view to a differing release of scents of different kinds for a specific purpose.

If an ultrasound generator is used to rupture the microcapsules, the rupturing process is very effective; the capsules may, therefore, be comparatively stable by nature, which facilitates storage and handling before use.

The development of the invention, according to other embodiments thereof is also advantageous with regard to effective rupturing of the microcapsules.

In a playback device according to another aspect of the invention, rupturing of the microcapsules in a specific region of the substrate always takes place completely, and the intensity of the scent is controlled by way of the forward feed of the substrate carrying the microcapsules. This is advantageous with regard to reliable release of the scents whilst at the same time being able to control the intensity of the scents very precisely.

In yet another aspect of the device, the light generation is mirrored acoustically.

If the light control unit is coupled to a playback device by an acoustic or optical (e.g. IR) modem, the generation of additional stimuli in the correct phase is obtained without intervention in the playback device. This additional unit can then be marketed as a self-contained unit which can easily be put into operation by technically less competent users.

This is made even simpler by combining the various sub-units in a common housing.

Yet another development of the invention allows additional visual stimuli, which can be varied over a wide range in terms of colour, pattern and intensity, to be generated using the television set found in any case in most households.

BRIEF DESCRIPTION OF THE DRAWING

The invention is described in detail below with the aid of embodiments and with reference to the drawings in which.

DETAILED DESCRIPTION OF THE PREFERRED EMBODIMENTS

Figure 1:
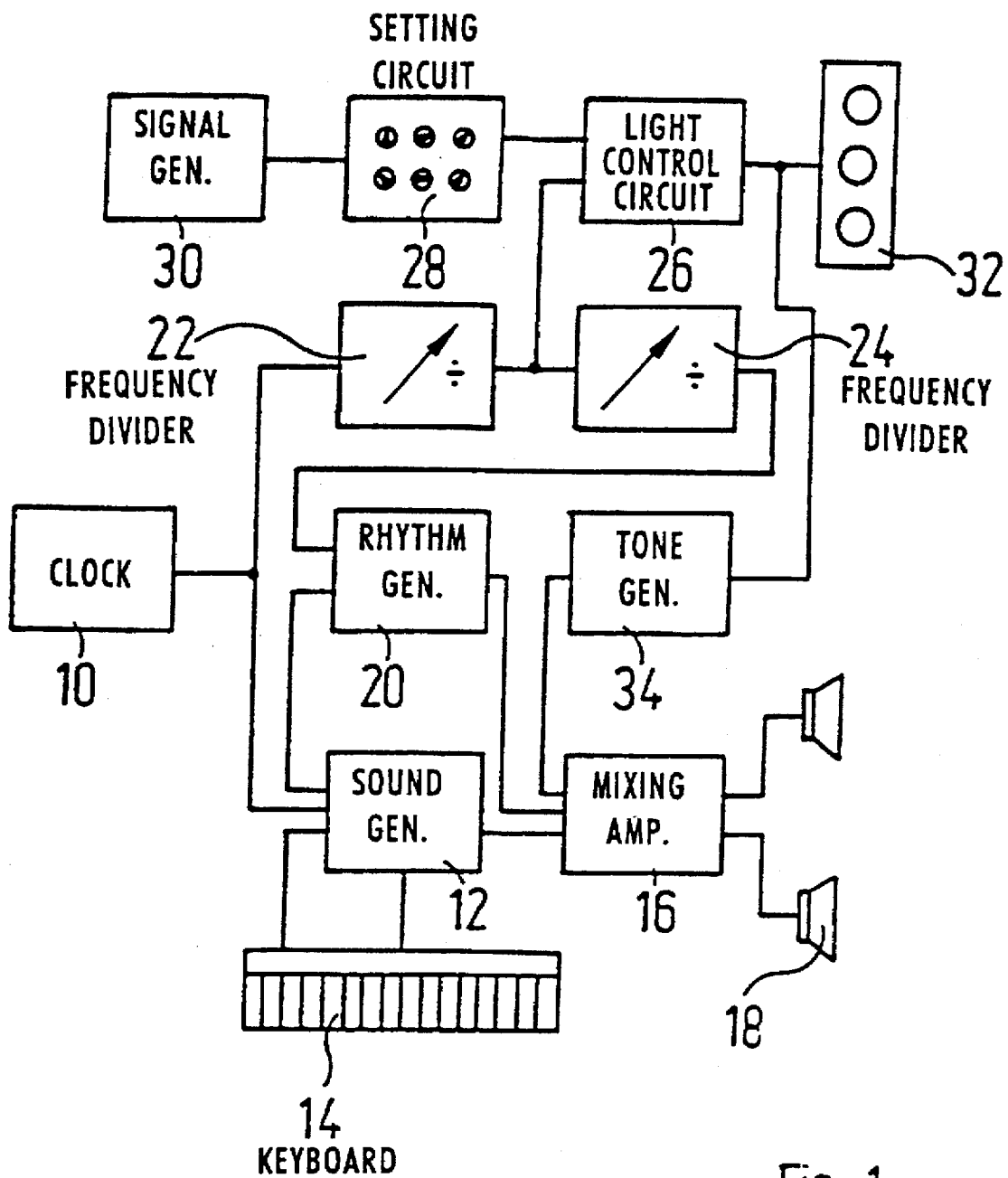
FIG. 1: is a block diagram of an electronic keyboard instrument additionally provided with a device for generating visual stimuli synchronously with but of a higher frequency than the musical accompaniment.

In FIG. 1, reference numeral 10 denotes a central clock for a keyboard. The clock provides the basic frequency for a sound generator 12 which in turn cooperates with a keyboard 14. The latter is provided with additional keys or buttons for setting musical accompaniment and/or kind of instrument, as is known per se.

The output of the sound generator 12 is connected to one of the inputs of a stereo mixing amplifier 16 which actuates loudspeakers 18.

A second input of the mixing amplifier 16 is connected to the output of a rhythm generator 20 which has two inputs. A first input receives a control signal supplied from the keyboard 14 and specifying the type of rhythm, and also a second control signal which is derived by two series-connected frequency dividers 22, 24 from the output signal of the clock 10 and which specifies the tempo frequency. The two frequency dividers 22, 24 have an adjustable dividing ratio, as indicated by arrows.

The connection line between the two frequency dividers 22, 24 is connected to one input of a light control circuit 26. The latter receives at its second input control signals provided by a setting circuit 28 and specifying the amplitude and colour of the light to be generated. The setting circuit 28 in turn receives a raw signal, provided by a signal generator 30, which varies according to a predetermined pattern. The signal generator may be a sine generator running at low frequency or a digitally operating voltage generator which, stored in a ROM for example, contains a slowly varying audio signal envelope.

In accordance with the control signals applied to its inputs, the light control circuit 26 generates light signals for a one-colour or multi-colour light generator 32, the frequency thereof being specified by the output signal of the frequency divider 22 and the amplitude thereof being specified by the setting circuit 28 and the signal generator 30.

It will be seen that, with the above-described electronic keyboard, there is obtained synchronously with the musical accompaniment, the time of which is set at the frequency divider 22 and 24, a generation of light pulses of a higher frequency in relation to the tempo, it being possible to set the relationship between the frequency of the light pulses and the time of the musical accompaniment at the frequency divider 24.

In addition, in the case of the keyboard shown in FIG. 1, provision is made for the light signals to be used to actuate a tone generator 34 which provides, for example, in the simplest case three correspondingly controlled sine pulse sequences of differing height. The tone generator 34 may, however, have a more complicated structure and provide in dependence upon the light signals, for example, broader spectrum tone signals reproducing, for example, triangles, wooden drums or the like. The output signal of the tone generator 34 is passed to a third input of the mixing amplifier 16 so that the light pulses generated by the light generator 32 are mirrored acoustically.

Figure 2:
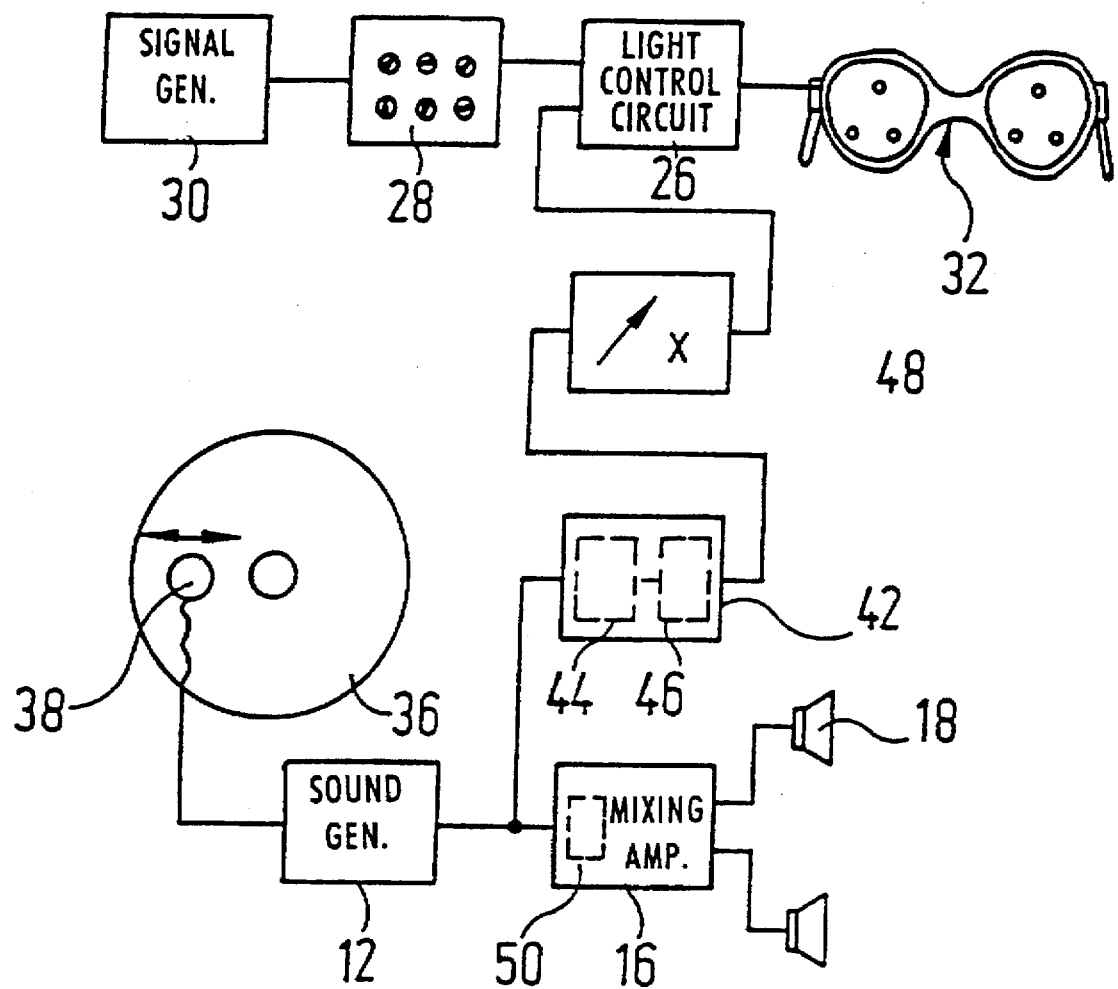
FIG. 2: is a block diagram of a CD player additionally provided with a device for the phase-synchronized generation of higher-frequency visual stimuli.

FIG. 2 shows schematically a CD player likewise provided with a device for generating higher frequency light pulses in the correct phase.

A compact disc 36 is turned by a drive not shown. Its recording tracks are read by a pick-up head 38 which is movable in the radial direction by a drive, also not shown.

The output signal of the pick-up head 38 actuates the sound generator 12, the output signal of which is again applied via the amplifier 16 to the loudspeakers 18.

The output signal of the sound generator 12 is passed to a special signal-shaping circuit 42 which can be formed, for example, by connecting a filter 44 in series with a Schmidt trigger 46 actuated by the output signal of the filter 44. If the filter 44 has been set to low frequencies, pulses having the frequency of the lower frequency accompaniment of the piece of music read by the pick-up head 38 are obtained at the output of the Schmidt trigger 46.

The output signal of the signal-shaping circuit 42 is again applied, by way of an adjustable frequency multiplier 48, to one input of the light control circuit 26. The second input thereof again receives the output signal of the signal generator 30 modified by the setting circuit 28. The light generator 32 is reproduced as a pair of spectacles having, on opaque lenses, in each case three light-emitting diodes for the three primary colours. If desired, it is again possible to generate light of a single colour only and to use for this only one light-emitting diode or several light-emitting diodes operating at the same wavelength.

There is thus obtained without appreciable intervention in the CD player a generation of light pulses that is in the correct phase relation to the accompaniment of a piece of music but has a frequency that is adjustable in relation to the time of the piece, normally a higher frequency.

As a modification of the embodiment described above, it is possible to use in the manufacture of the compact disc or gramophone record or music cassette a mixing stage to one input of which the music audio signal is applied while the other input receives purely sine signals modulated in accordance with the control commands for the light generator. The control signals so recorded concurrently are then used again by the appropriately tuned signal-shaping circuit 42. At the same time, these control signals can be heard in the loudspeakers, with the result that simultaneous visual and acoustic stimuli are again obtained. If this is not desired, a blocking circuit 50 which blocks off the sine-shaped light control signals can be provided at the input of the amplifier 16.

Figure 3:
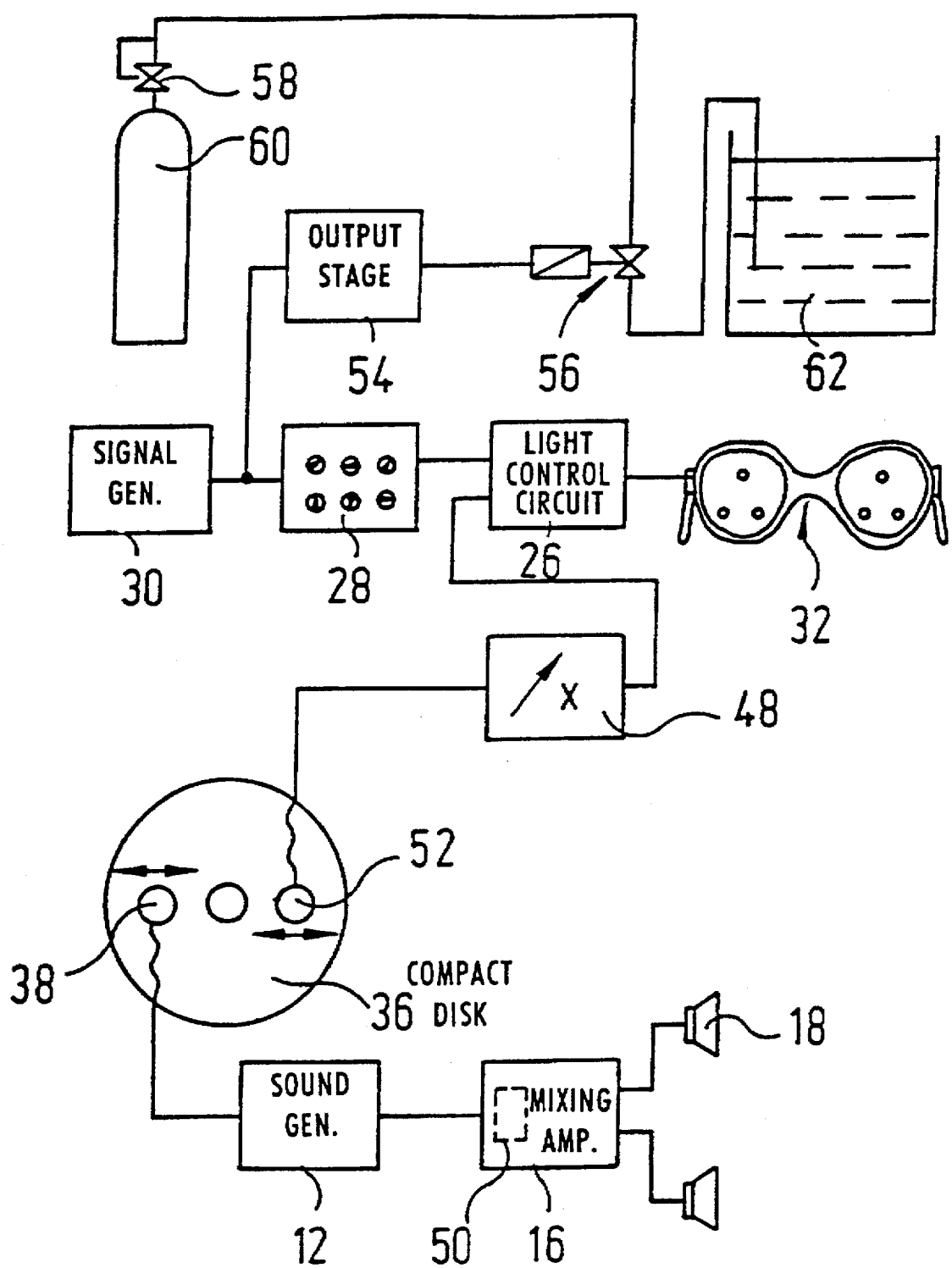
FIG. 3: is a block diagram similar to that shown in FIG. 2, which, however, shows a modified CD player in which, at the same time, a device for the controlled release of scents is provided.

In the embodiment shown in FIG. 3, parts of the device that have already been described above are again provided with the same reference numerals and will not be described in detail once more.

On the compact disc 36, the control signals for the light generator 32 are stored on a separate recording track and this is read by a second pick-up head 52. The output of the pick-up head 52 either is connected directly to the input of the frequency multiplier 48, as shown, or, when a higher frequency is selected for the control signal, is connected directly to the input of the light control circuit 26.

In addition, provision is made for a solenoid valve 56, which is connected by way of a pressure regulator 58 to a compressed air bottle 60, to be operated by the slowly varying output signal of the signal generator 30 by way of an output stage 54 which at the same time converts the amplitude-modulated envelope signal into a correspondingly pulse-duration-modulated scent control signal. A line attached to the outlet of the solenoid valve 56 is immersed in a volume 62 of liquid scent, so that, by controlling the rate at which the air bubbles through, scents are released in a controlled manner.

In this manner, a release of scents is obtained synchronously with the slow variation of the amplitude of the light pulses.

Figure 4:
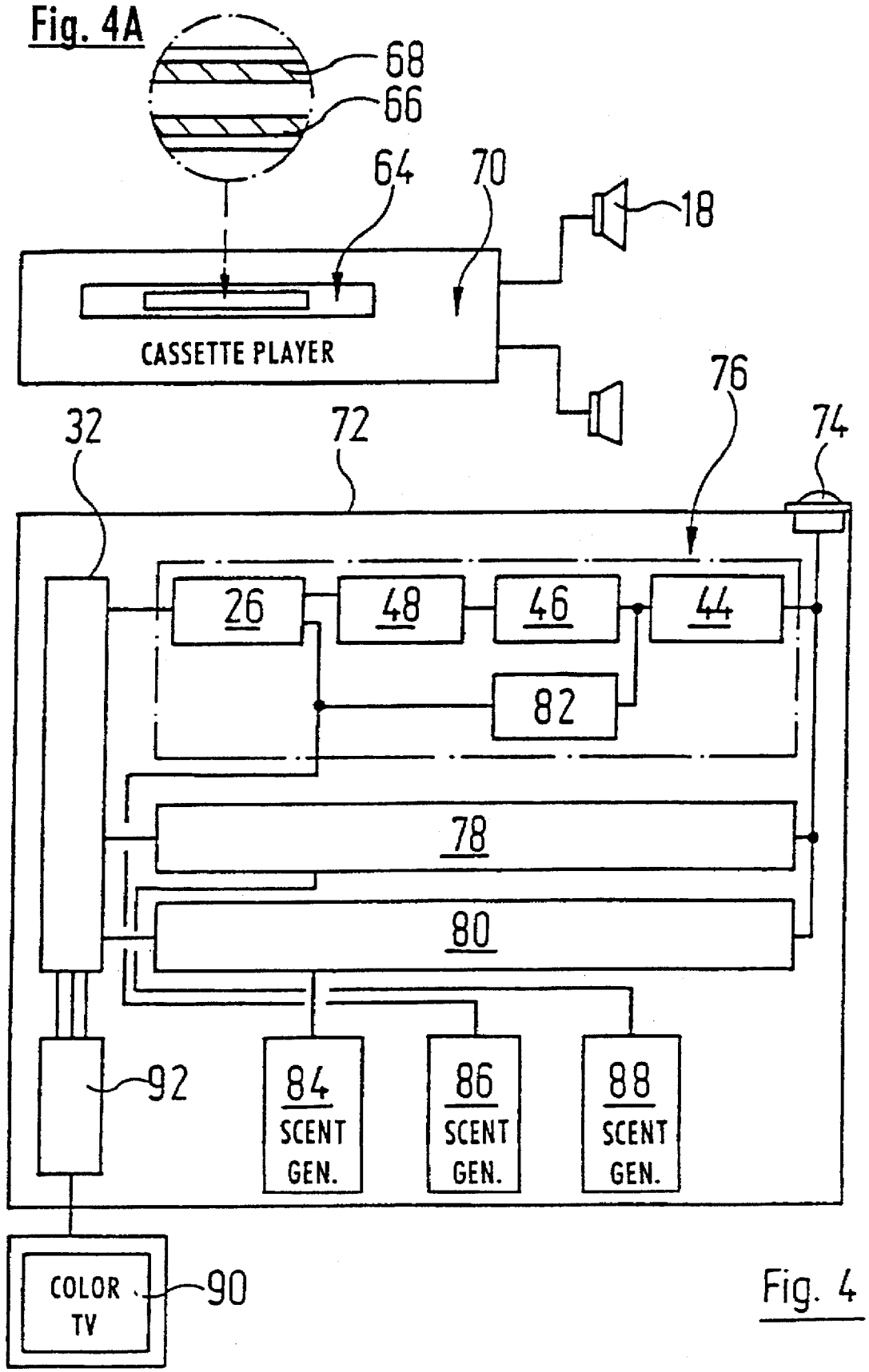
FIG. 4: is a block diagram similar to that shown in FIG. 2, showing a further modified recreational device.

In the modified illustrative embodiment shown in FIG. 4 there is used as the sound-recording medium a music cassette 64 in which one of the two stereo sound tracks 66, 68 is used for recording the music while the other is used for recording control signals for, for example, three different light sources. These three light signals lie in distinctly separate audible ranges of the spectrum, for example at standard pitch, at $c^1$ and at $f^1$. These signals are amplitude-modulated and are passed to the loudspeakers 18 again by way of one of the stereo channels of the associated cassette player 70 which is shown merely schematically.

Arranged in a housing 72 is a microphone 74 which by way of control channels 76, 78, 80 actuates a three-colour light generator 32. These may each consist of a series-connection of a filter 44, a Schmidt trigger 46, a frequency multiplier 48 and a light control circuit 26, as described in detail above with reference to FIG. 2.

Instead of a separate envelope generator, in the recreational device shown in FIG. 4 the signal obtained at the outputs of the filters 44 of the various control channels 76, 78, 80 is rectified in rectifier circuits 82 and, with the resulting slowly varying envelope of the light signals, the amplitude of which was specified when the light signals were played onto the sound track 68, apart from the light control circuits 26, controllable scent generators 84, 86, 88 are additionally actuated to release various scents.

In addition to the three-colour light source 32, a colour television 90 is actuated via a signal converter 92 by the light signals passed through the light generator 32. The signal converter 92 converts the light signals into suitable video signals, similar to those emitted, for example, by a video camera or a video recorder.

The use of the colour television set 90 as a controllable light source has the advantage that a very large number of colours can be set very precisely with regard to colour tone, intensity and frequency and, where applicable, with regard to pattern. This use of a colour television set which is in any case present in most households, as a controllable light source of great variability thus causes the user no additional costs.

As a modification of the embodiment shown in FIG. 4, the light generator 32 can also be omitted and the colour television 90 can be used as the sole source providing visual stimuli.

Figure 5:
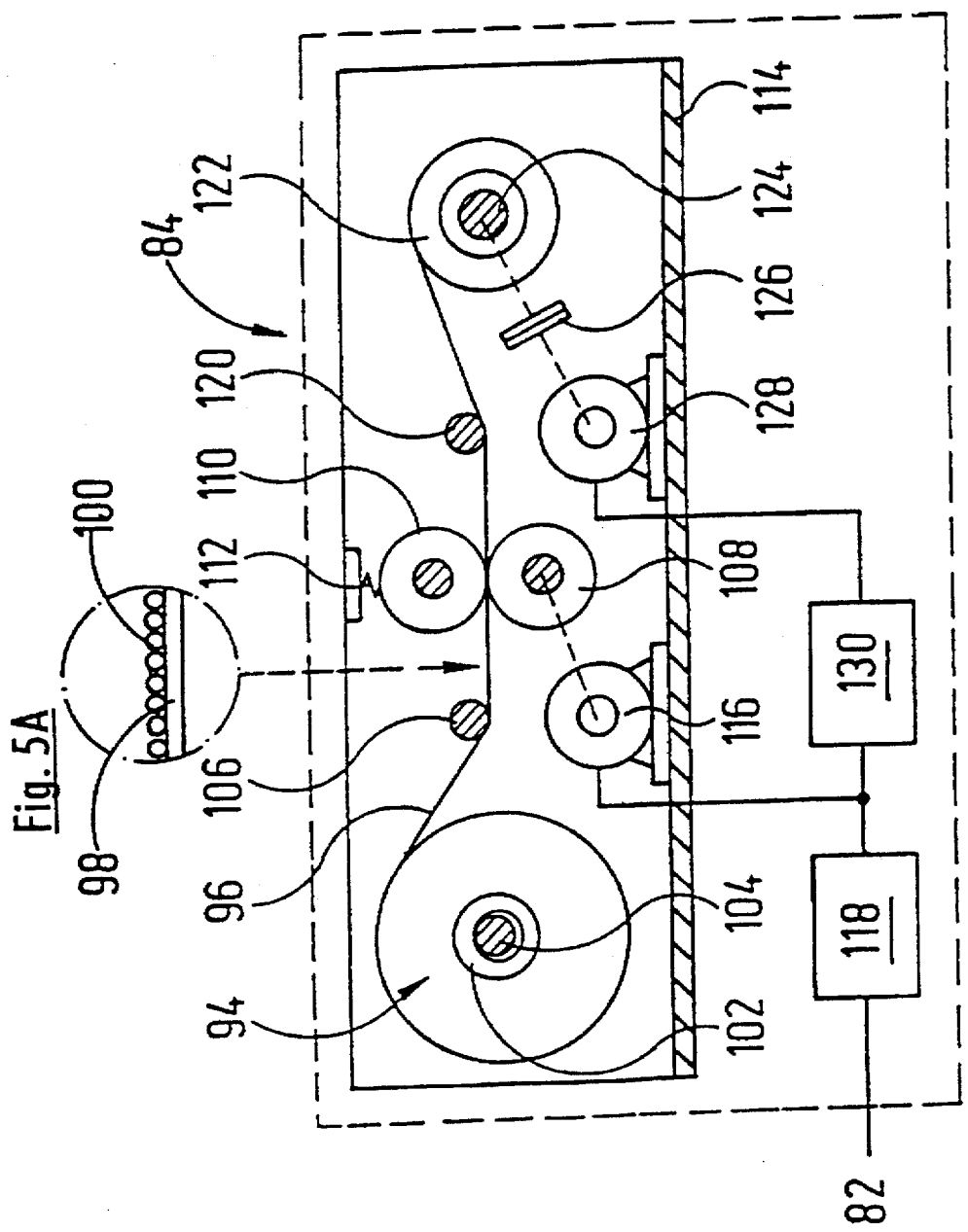
FIG. 5: is a schematic representation of a controllable scent source of the kind used in the recreational device shown in FIG. 4, one side panel of a device housing having been broken away.

As will be seen from FIG. 5, the scent generator 84, and accordingly the scent generators 86, 88, each have a supply reel 94 of a scent carrier web 96 which consists of a web of paper 98 with microcapsules 100 attached thereto and is wound onto a core 102. The microcapsules may consist, for example, of gelatin and contain a scent.

The supply reel 94 is mounted to be freely rotatable on a shaft 104. The scent carrier web 92 runs over a guide roller 106 into cooperating squeezing rollers 108, 110. The squeezing roller 110 is movable in the vertical direction and is biassed by lateral springs 112 towards the squeezing roller 108 which is fixed in position in a frame 114.

The fixed squeezing roller 108 is driven by a motor 116 which receives the rectified output signal of the associated filter 44 via an output stage 118.

The used scent carrier web 96 runs over a further guide roller 120 onto a core 122 (left from a previously used supply reel) which is rigidly mounted on a shaft 124. The latter is driven via a sliding clutch 126 by a motor 128 which is activated by a supply circuit 130. The latter operates in dependence upon the output signal of the output stage 118, so that the motor 128 is driven together with the motor 116 but at a different speed.

In the embodiment shown in FIGS. 4 and 5, a controlled release of different scents is thus obtained according to the amplitude of the light control signals recorded on the sound track 68.

As a modification of the embodiments described above, it is also possible to use in a recreational device a mixture of controllable scent sources shown in FIG. 3 and controllable scent sources shown in FIG. 5. In a recreational device shown in FIG. 3 it is also possible to use as the carrier gas which bubbles through the scent 62 oxygen or oxygen-enriched air. It will be understood that a small compressor can be used instead of a compressed air bottle.

It is also possible to use instead of a compact disc or a music cassette a conventional gramophone record as the medium for the audio signals and, where appropriate, the light signals.

Figure 6:
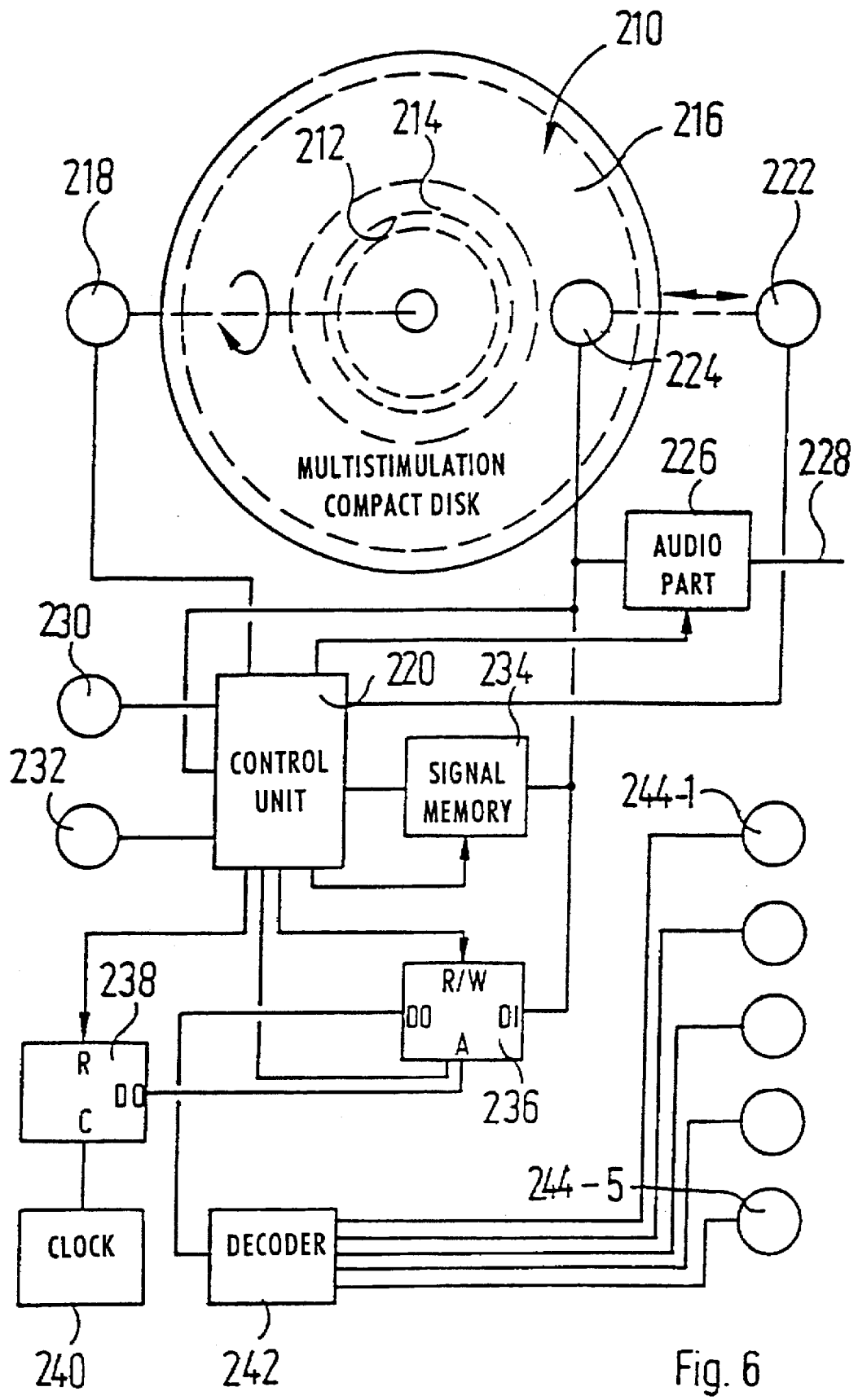
FIG. 6: is a block diagram of a playback device for compact discs together with a multi-stimulation compact disc.

In FIG. 6, reference numeral 210 denotes a multi-stimulation compact disc on which three different recording regions are defined: a track region 212 which contains the title information and organisation data, a track region 214 which contains control signals for stimulus generators, as will be described in more detail hereinafter, and a track region 216 which contains the audio signals.

A motor 218 energised by a control unit 220 is provided for rotating the compact disc 210. The control unit 220 further energises a linear drive 222 by which a reading head 224 is moved in the radial direction over the compact disc 210.

The reading head 224 is connected to the input of an audio part 226 that is of a construction usual for CD players and that provides on a line 228 input signals for an amplifier. The line 228 is in practice a multi-wire line for the left and right stereo channel, which does not need to be explained in detail here, however. Other lines shown in FIG. 6, especially lines for transmitting digital signals, are in practice multi-wire lines or data buses, which also does not need to be explained in detail here, however.

The control unit 220 controls the audio part 226 roughly speaking by suppressing it when the reading head 224 is over the track region 212 or the track region 214 or when no signals are being read from the compact disc 210 at all.

The control unit 220 operates for its part in dependence upon a sensor 230 which responds when a new compact disc is loaded into the playback device. Further connected to the control unit 220 is an entering unit 232 which is used for manual selection of the operation of the playback device, for example for playing a specific title. Another input of the control unit 220 is connected to the output of the reading head 224 so that the control unit 220 is able to recognise when the signals emitted by the reading head 224 represent title data, organisation data or control signals.

There is also connected to the output of the reading head 224 an organisation signal memory 234 which stores the title and organisation data when the reading head 224 is moved over the track region 212 after loading of a compact disc 210. Activation of the organisation signal memory 234 for reading in those data is effected by the control unit 220.

A control signal memory 236 is also connected to the reading head 224. When data are being read in, it is addressed by the control unit 220 which places the control signals for the various pieces recorded in the track region 216 in separate memory arrays.

Within the control signal track region 214, the control signal sequences for the individual pieces of music are separated by separating signals each comprising a character sequence additionally characterising the allocation. Instead or in addition, the control signal sequences for the various pieces of music can be stored in sectors and tracks specifically assigned to a piece of music of a particular No., so that allocation is also possible by sector and track number.

The control signals stored in each memory array contain all the information on how a plurality of stimulus generators are to be activated in a slowly varying manner throughout the course of the associated piece of music. The quantities of data required for this are only small: assuming a time resolution of only 10 sec is desired, with a typical total playing time of a compact disc of 90 min maximum and with a stimulus generator being actuated by 16-bit long commands, only about 1 kB of memory is required per stimulus generator. Thus, an inexpensive, commercially available RAM of 64 kB is sufficient for storing all the control commands for a large number of stimulus generators.

Reading of the control signal memory 236 is effected in accordance with the output signal of an addressing counter 238 which is reset by the control unit 220 at the beginning of each piece of music. The output signal of the addressing counter 238 forms the least significant part of the complete address of a control signal memory cell; the most significant address part, which identifies the memory array, in other words the particular piece of music, is also provided during the reading operation by the control unit 220.

The addressing counter 238 is connected at its counting terminal to a free-running clock 240 which operates, for example, with a frequency of 0.1 Hz. If stimulus generators that operate only with great inertia are among the stimulus generators actuated, that frequency can be reduced still further.

The control signals read from the control signal memory 236 pass to a decoder 242 which determines from the first part of the control signal the particular stimulus generator that is to respond and provides the remainder of the control signal via an output line associated with that particular stimulus generator. Connected to those output lines are various stimulus generators 244-i, namely:

- a controllable light source 244-1 which, in practice, may be, for example, a standard lamp with a controllable dimmer, or a louvre blind wherein the inclination of the louvres can be controlled electrically, an electrically operated curtain or a light organ;
- a tactile stimulus generator 244-2 which may, for example, be a servo adjuster for the arms and/or seat and/or foot rest of an armchair, a massage device built into an armchair, or the like;

a scent generator 244-3 which releases a scent with the desired intensity in dependence upon the control signals transmitted;

an acoustic stimulus generator 244-4 which may, for example, be another playback device which is slowly varied in its mode of operation (by this means it is possible, for example, to give the impression of an "encounter" with another sound world, similarly to that obtained, for example, in a concert café (background noises overlie the music) or when travelling past a fairground with the car radio switched on); or a visual stimulus generator 244-5 that is controllable in its mode of operation, for example a controllable fan that sets leaves of a house plant or a mobile in motion.

It will be appreciated that a plurality of different stimulus generators of each category can also be provided.

Another modification of the embodiment shown in FIG. 6 may comprise using as the recording medium not a compact disc for music or spoken word but a video disc, in which case the audio part 226 is then replaced by an audio/video part.

In the embodiment shown in FIG. 6, the control signals for all pieces of music recorded were stored together in the track region 214. The control signals for the various pieces are separated either by separating and identification marks interspersed between them or by allocating given sectors of the control signal tracks to the various pieces of music.

Figure 7:
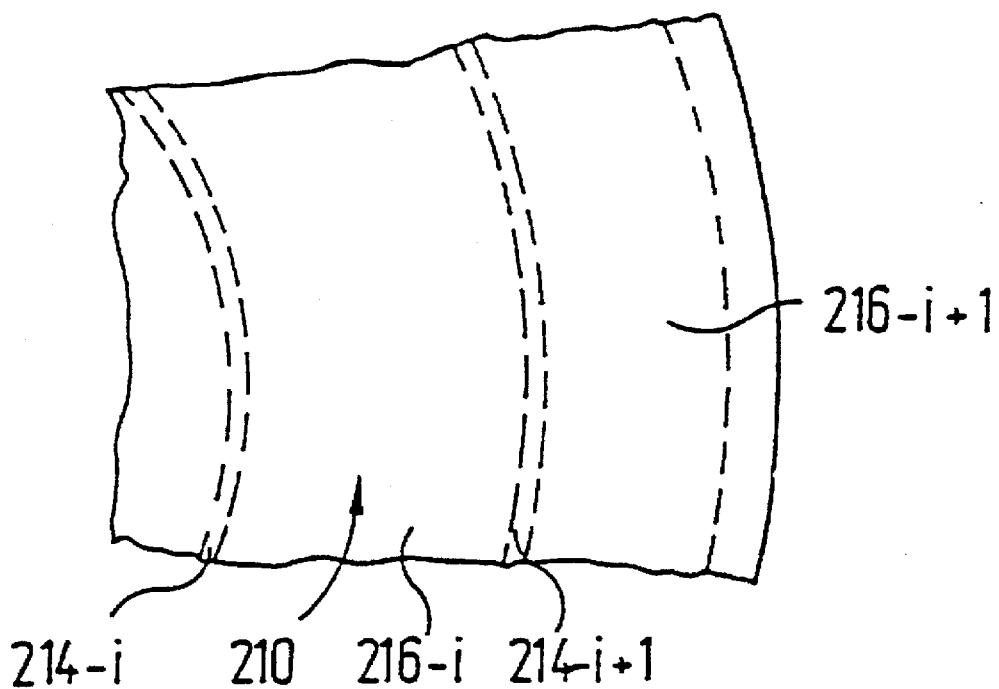
FIG. 7: shows a portion of a modified multi-stimulation compact disc.

In the modified embodiment shown in FIG. 7, the sub-regions 216-1, 216-2 etc. of the track region 216 each allocated to a piece of music are each preceded by the associated sub-region 214-1, 214-2 etc. of the control signal track region 214. Thus, at the beginning of every piece of music, the associated control signals are automatically read in first. The control unit 220 recognises those control signals by corresponding command code prefixes and passes the control signals into the control signal memory 236 as in the embodiment shown in FIG. 6. With the interleaving of the track regions 214 and 216 shown in FIG. 7, however, the control signal memory needs to have only a smaller capacity or, rather, for a given memory size, a higher time resolution for the actuation of the stimulus generators 244 is obtained. Reading of the control signals from the control signal memory 236 is also simplified; the addressing of the memory cells is carried out entirely by the addressing counter 238.

In the embodiments shown in FIGS. 6 and 7, it is assumed that the recording medium is a compact disc and that the audio signals are accordingly recorded on concentric tracks. It will be appreciated that the principle described can equally be applied to recording media in tape form, the analogue of the embodiment shown in FIG. 6 being first a block of title and organisation data at the beginning of the tape, then a block with all the control signals and, following this, the blocks with the various pieces of music. When the tape is played from the beginning, first the title and organisation data, then all the control signals and then the successive pieces of music are read out. The stimulus generators can be actuated with the same electronics and in the same manner as described with reference to FIG. 6.

The embodiment shown in FIG. 7 can also be translated analogously to recording media in tape form: recorded before each piece of music is the group of control signals required to actuate the various stimulus generators in the period for which the piece of music plays.

Figure 8:
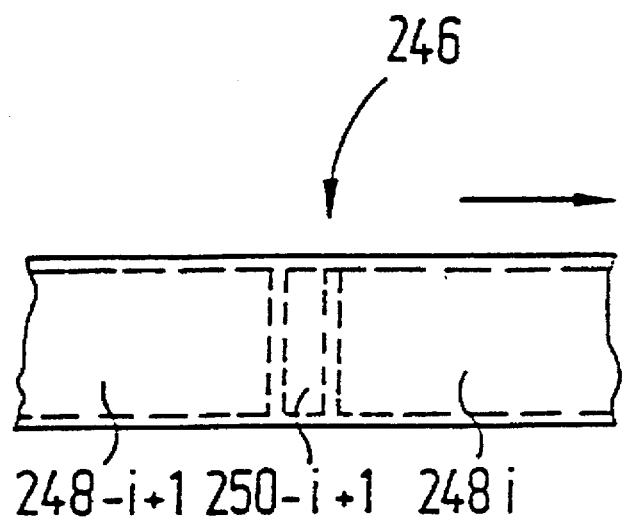
FIG. 8: is a schematic view of a portion of a multi-stimulation magnetic tape.

FIG. 8 shows schematically a further modified method of recording the control signals on a magnetic tape 246. Inserted between relatively long audio signal sub-blocks 248-i of a piece of music are short control signal blocks 250-i the beginning and end of which are each marked by marking signals. A magnetic tape of this kind can be read out using electronics modified only slightly in comparison with FIG. 6: one output of the control unit 220 is directly connected to the input of the decoder 242, and the circuits 236 to 240 are omitted. The control unit 220 operates in such a way that, when it recognises a control signal block 250, it passes it on to the decoder 242 and, for that brief period, blocks the audio part 226.

Figure 9:
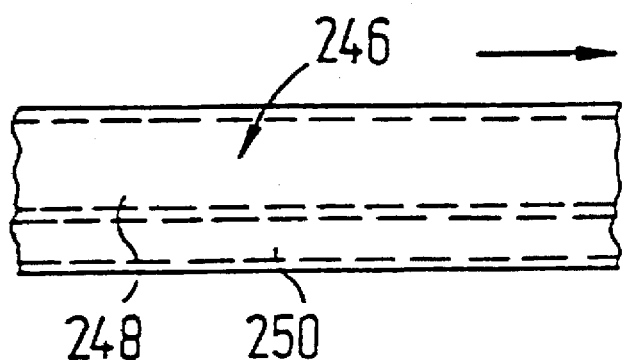
FIG. 9: is a schematic plan view of a modified multi-stimulation magnetic tape.

As a further modification of the invention, according to FIG. 9 it is possible to provide in addition to a continuous audio signal track 248 a parallel continuous control signal track 250 that is read by a separate reading head. The output of the reading head can then be connected (if necessary with the interposition of suitable signal-shaping circuits) directly to the input of the decoder 242.

It will be appreciated that the interleaving of audio signal recording with control signal recording as described for magnetic tapes with reference to FIGS. 8 and 9 can also be provided analogously for rotating recording media.

It will also be appreciated that the present invention can also be used in connection with recording media other than those already discussed, for example with conventional sound films in which the control signals are incorporated in the sound track or are provided on a separate control signal track or are accommodated in a leader portion of the film, for example in a number of frames which are read out by means of an array of diodes or a solid-state image converter when the film is stationary or moving slowly. Other recording media that come into consideration are minidiscs, CCDs.

Figure 10:
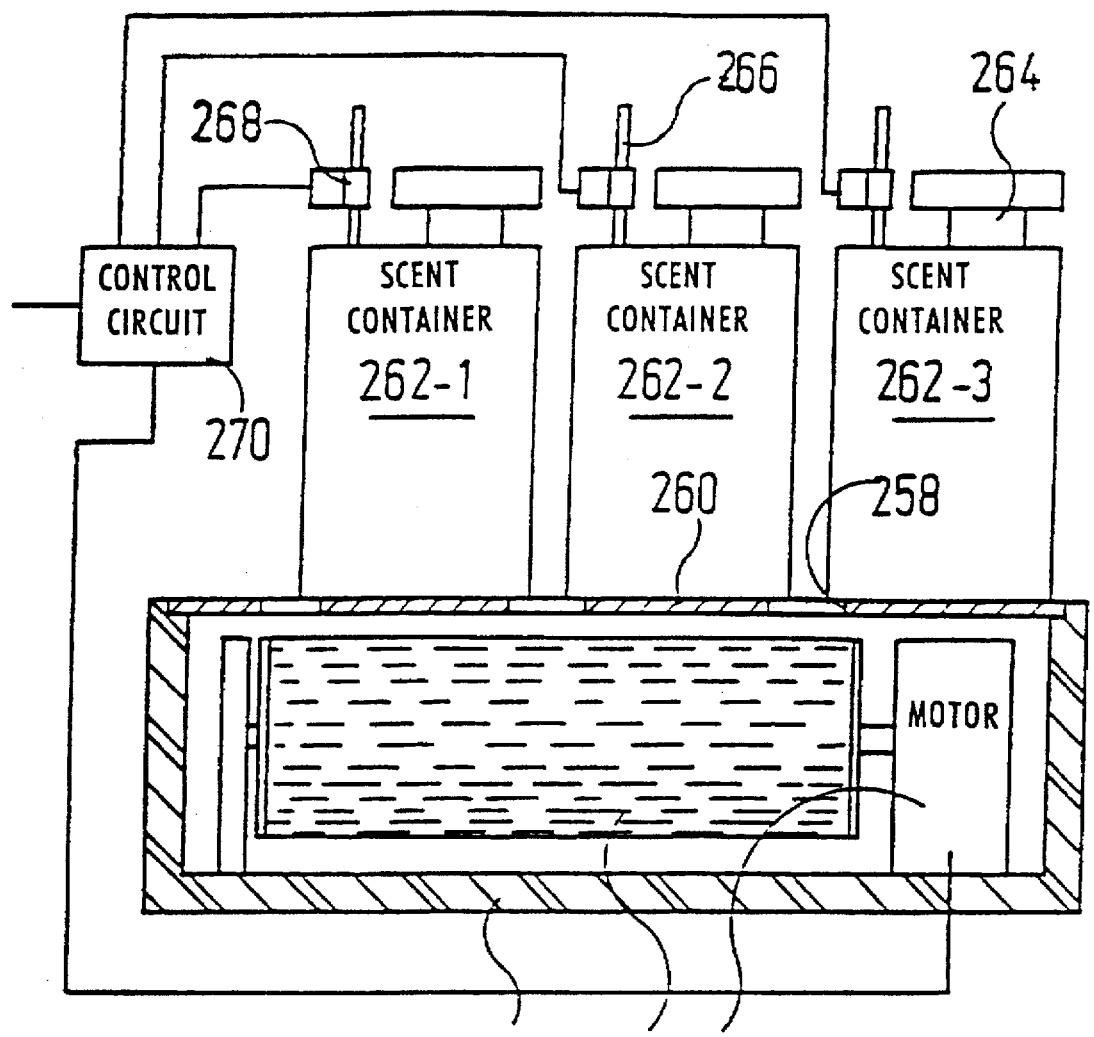
FIG. 10: is a schematic representation of a controllable scent generator for three different scents.

FIG. 10 shows an embodiment of a scent generator that is able to release in a controlled manner three different scents. Arranged in a housing 252 is a tangential fan 254 which is driven by a motor 256. The air delivered by the tangential fan 254 passes through circular-arcuate openings 258 in a cover plate 260 of the housing 252. Three scent containers 262-1, 262-2 and 262-3 holding liquids containing different scents stand on the circular portions of the plate remaining between the openings 258. The head space above the level of the liquid of the scent containers 262 can be placed under pressure by means of a pump 264 indicated merely schematically in the drawing. Immersed in the volume of liquid is the lower end of a spray tube 266, the delivery end of which can be opened and closed by a solenoid valve 268. The solenoid valves 268 are actuated in a pulse-duration-modulated manner to control the intensity of the scent released. This is provided by a control circuit 270 which receives at one input the scent control signal of the decoder 242. As soon as any scent control signal is present, the control circuit 270 sets the motor 256 in operation. According to the type of scent control signal transmitted, the control circuit 270 then determines which of the solenoid valve(s) is(are) to be actuated and how the relationship between open time and closed time is to be set. The scents released by the spray tubes 266 are rapidly conveyed into the surroundings by the curtain of air produced by the tangential fan 254.

In practice, a considerably larger number of scent containers than three can be used, for example from thirty to fifty scent containers. The scent containers may furthermore be combined to form a block in practice, with only a single common plug being provided for the various solenoid valves. The entire scent container unit can then be operated and replaced in that form.

Figure 12:
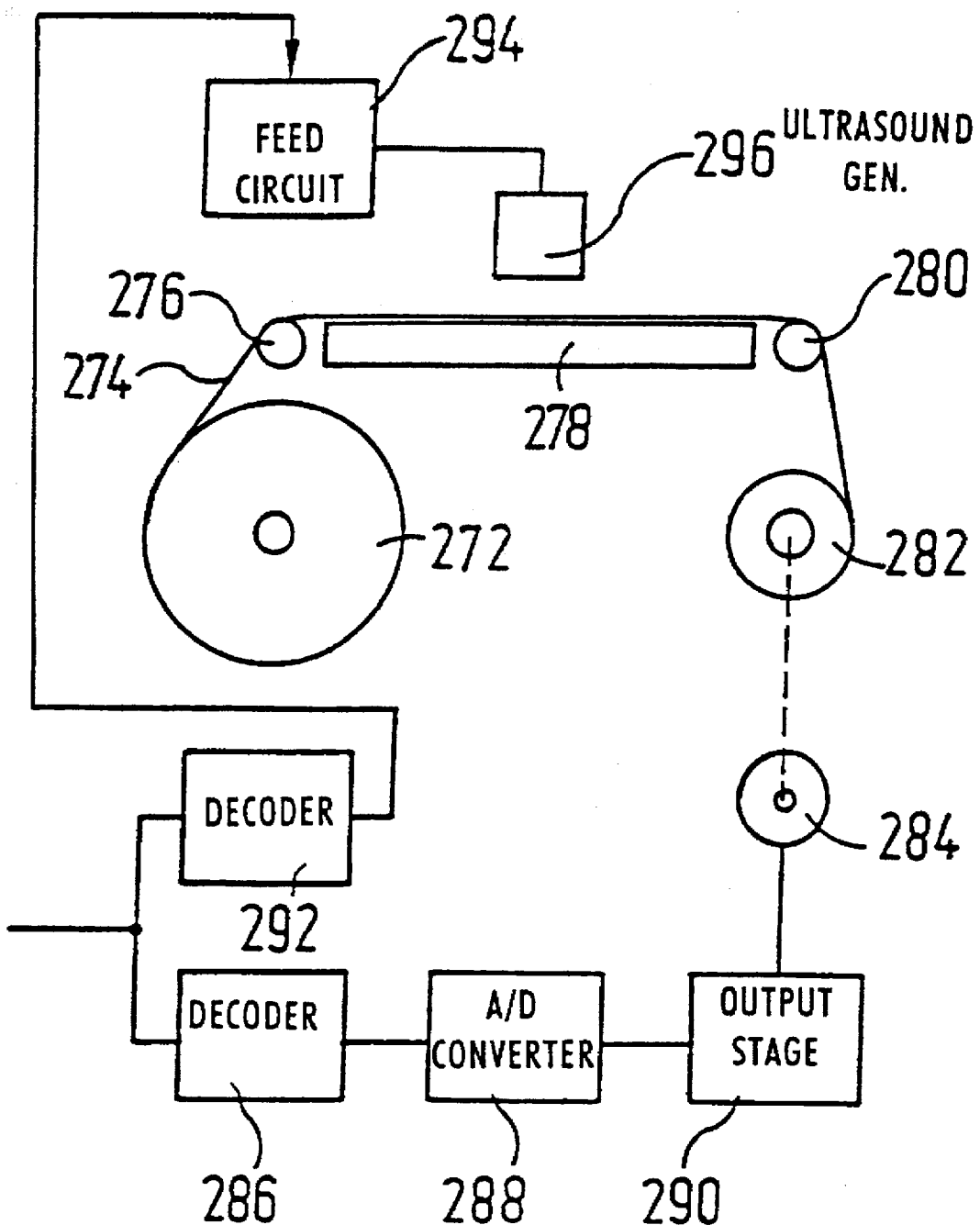
FIG. 12: is a schematic representation of a scent generator that can be used together with a scent carrier tape shown in FIG. 6.

FIG. 12 shows a modified scent generator. A carrier tape 274 impregnated with scents is passed from a supply reel 272 over a deflection roller 276, a support plate 278 and a further deflection roller 280 to a take-up reel 282. The axis of the latter is driven by a motor 284 which is driven by way of a decoder 286, to which the scent control signal is applied, a digital-to-analogue converter 288 connected downstream, and an output stage 290, in accordance with the intensity of scent release required by the control signal.

Connected to the input terminal of the scent generator is a further decoder 292 which provides an output signal whenever a release of scent other than zero is required. The output signal of the decoder 292 actuates a feed circuit 294 for an ultrasound generator 296. The latter is arranged above the carrier tape 274, so that the scent-containing microcapsules provided on the carrier tape 274, which can be broken open by sound, can be ruptured by the sound waves which it generates.

Figure 11:
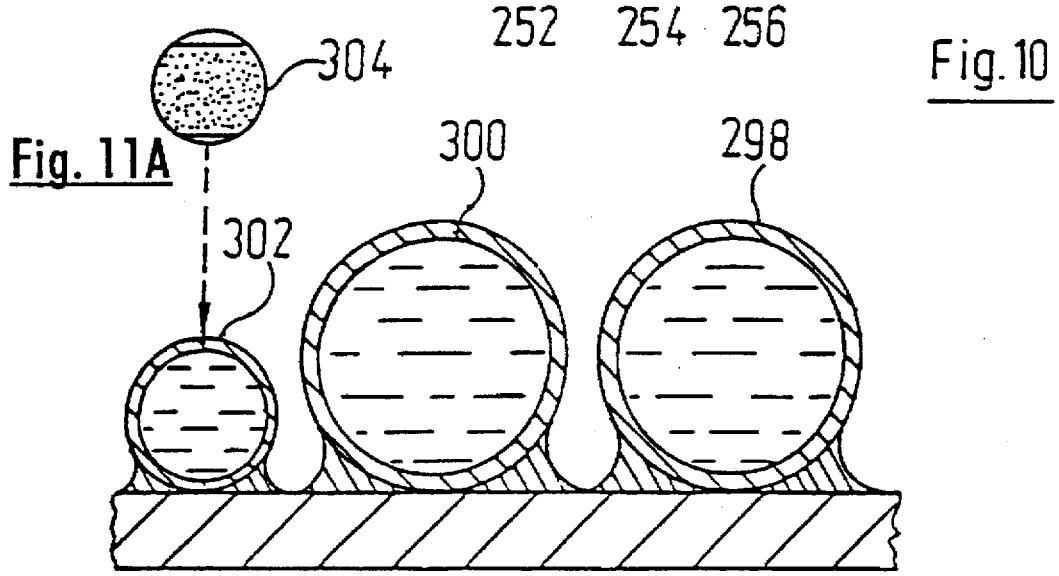
FIG. 11: shows a schematic enlarged section through a scent carrier tape.

As will be seen in FIG. 11, the scent impregnation of the carrier tape 220 consists of a mixture of different microcapsules. The drawing shows at 298 a first type of microcapsule which has a large diameter with a small wall thickness and can, therefore, be ruptured by sound waves relatively easily. At 300, microcapsules are shown which correspond to the microcapsules 298 in diameter but have greater wall thicknesses and are therefore more difficult to rupture.

Shown at 302 are microcapsules of smaller diameter which have a porous wall material as shown in the enlargement at 304. The porosity of the wall material is, however, slight, so that only small amounts of scent diffuse through the wall in the absence of external influences. When loaded in alternating manner by a sonic field, however, the capsule wall acts similarly to a pump diaphragm, so that scent passes through.

In a modified and simplified embodiment, microcapsules that can be ruptured by sound with different degrees of ease and that are filled with different scents can be provided. If, in this case, the mechanical stability of the microcapsules is selected to be small overall, they may also be ruptured by audible sound, so that a paper impregnated with microencapsulated scents can be placed directly in front of the loudspeakers of a stereo system and the different types of microcapsule can be ruptured one after another by means of the loudness.

Figure 13:
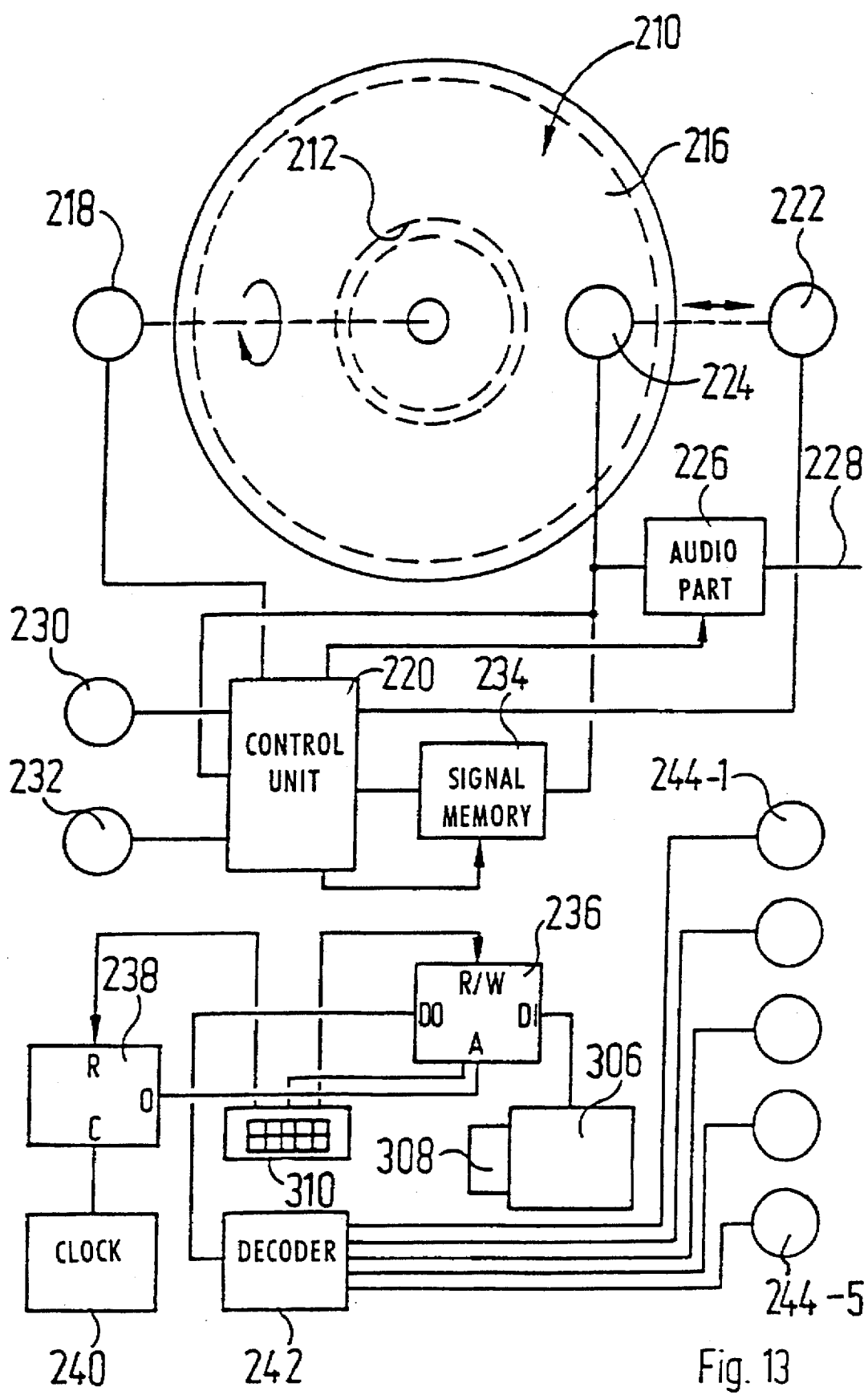
FIG. 13: is a representation similar to that shown in FIG. 6, in which a normal compact disc is used and a separate entering device is provided for stimulus generator control signals.

The modified embodiment shown in FIG. 13 corresponds in large part to that shown in FIG. 6. Corresponding parts are again provided with the same reference numerals and will not be described again in detail.

The control signals are read into the control signal memory 236 in this case by a card reader 306 which cooperates with a control signal card 308. The card may be a magnetic card, a punch card or a card carrying a ROM. Stored on the control signal card 308 are all the control signals that were provided in the control signal track region 214 of the compact disc 210 in the embodiment shown in FIG. 6. That region has been omitted in the embodiment shown in FIG. 13, that is to say, the compact disc 210 is a customary commercial compact disc.

The switching of the control signal memory 236 between reading in and reading out, the resetting of the counter 238 and the calling up of the various memory arrays of the control signal memory 236 is carried out by means of an entering panel 310 which accordingly replaces the control unit 220 since the function thereof exceeds the function of a normal CD player control unit.

As a modification of the embodiment shown in FIG. 13, the reading device can be replaced by an entering panel on which the control signals are entered manually.

Figure 14:
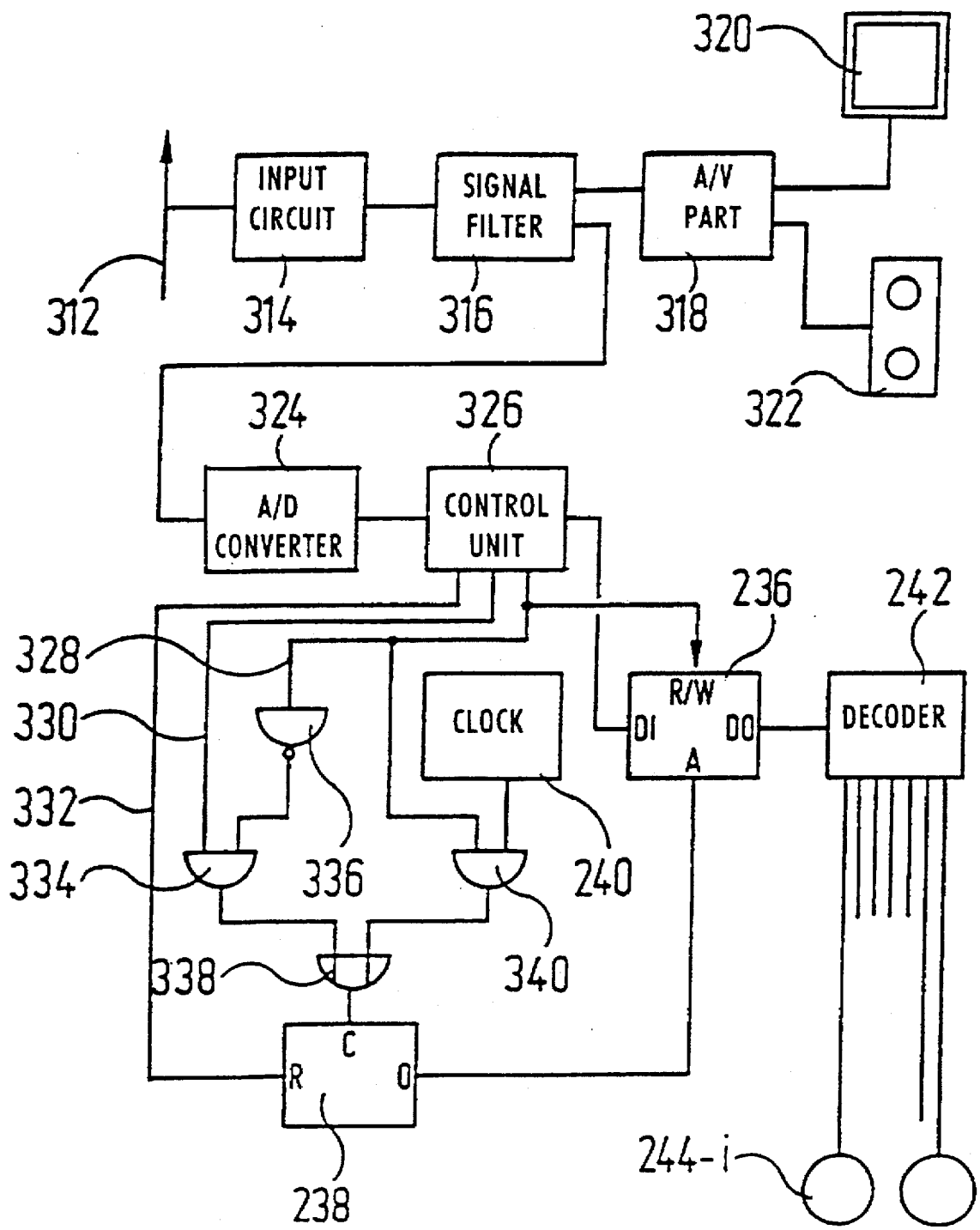
FIG. 14: is a block diagram of a television set provided with an accessory device for generating slowing varying sensory, tactile and other stimuli.

In the further modified embodiment shown in FIG. 14, the control signal memory 236 is actuated for the readout operation similarly to the embodiment shown in FIG. 6, namely by a slowly incrementing counter 238. The control signals themselves are, however, derived directly from the video signals received by a television receiver from an antenna 312. An input circuit 314 which demodulates the signals is connected to the antenna. Connected to the output of the input circuit is a control signal filter 316. At one output of the latter the normal audio and video I.F. signals are passed on to an audio/video part, designated 318 overall, which operates on a screen 320 and loudspeakers 322. At the second output of the control signal filter 316 control signals for stimulus generators 244-i are obtained. Filtering by the control signal filter 316 roughly speaking takes the form of the filter extracting from the stream of signals signal sequences that start and end with a special separating signal. The signals that have been filtered out are converted in an analogue-to-digital converter 324 into binary signals which then pass to a control unit 326. By reference to the separating signals the control unit first establishes when a transmission of control signals begins and ends. A corresponding control signal is provided on a line 328. That signal causes the control signal memory 236 to switch between writing (W) and reading (R). On another line 330 the control unit 326 provides a signal whenever a new control signal, for example comprising 1 or 2 bytes, has been received. On another line 332 the control unit 326 provides a signal at the beginning of a control signal packet and at the end of a control signal packet. That signal resets the counter 238.

An AND element 334 receives the timing signals present on the line 330. Applied to its second input via an inverter 336 is the activating signal of the line 328. The output of the AND element 334 is connected to a first input of an OR element 338 the output of which is connected to the counting terminal C of the counter 238. A second input of the OR element 338 receives via an AND element 340 the output signals of the free-running clock 240. Applied to the second input of the AND element 340 is the signal on the line 328.

Accordingly, during writing into the control signal memory 236, the counter 238 is incremented by 1 whenever a new control signal has been received. When reading from the control signal memory 236 the counter 238 is incremented according to the pulses of the clock 240.

The data input terminal DI of the control signal memory 236 is connected to an output terminal of the control unit 326 at which the digitalized control signals are emitted. A data output terminal DO of the control signal memory 236 is again connected to the decoder 242 which selects the various scent generators 244-i and passes the appropriate control signals to them.

The television set described above operates as follows:

The control signals for the stimulus generators 244-i are preferably combined to form a block corresponding to the contents of the control signal track block 214 in the embodiment shown in FIG. 6. This block is broadcast at the beginning of a broadcast transmission in a frequency gap and is separated by the control signal filter 316. The control signals are then stored in the control signal memory 236 as described above. After the control signal block has been transmitted, the counter 238 is reset by the control unit 326 and the control signal memory 236 is then read slowly as explained in detail with regard to the embodiment shown in FIG. 6. Thus, the stimulus generators are switched on at the desired points of the following broadcast transmission with the intensity desired in each case.

Figure 15:
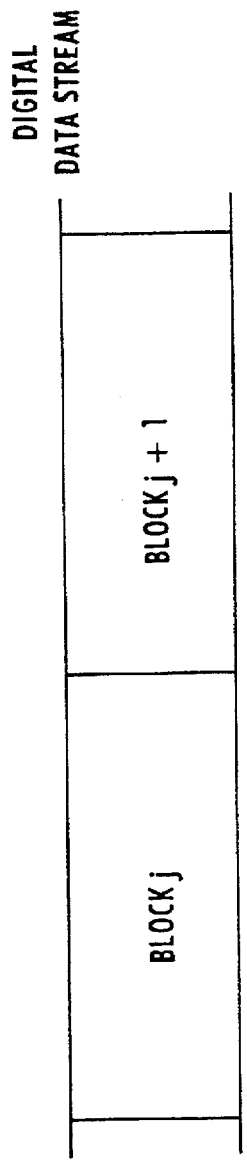
FIG. 15: is a schematic representation of a portion of the digital data stream of a recording medium for a digitalized audio signal.

The data stream shown in FIG. 15 is recorded on a digital sound medium, for example a disc or a magnetic tape cassette, or on the accompanying sound track of a video medium, for example a video disc or a video tape cassette. The data stream consists of serial data blocks (=fixed time intervals) of which data blocks j and j+1 have been indicated in FIG. 15 in order to illustrate the serial block sequence. Each data block has the structure shown in FIG. 16 in which the beginning of each data block is identifiable by the synchronizing information "Sync" provided as the "Header". In the case of uncompressed 16-bit linear-coded audio signals (for example in CDs or DAT cassettes) the "Sync" header is immediately followed by a sequence of sampling values of the digitalized audio signal. In the case of the data-compressed audio signals shown in FIG. 16 (for example minidiscs or DCC cassettes), a section "bit allocation information" and a section "scaling factors" is inserted between the "Sync" header and the sequence of sampling values.

Following the section "sampling values", a section for additional information is reserved in every data block. If no additional information is provided, logic zeroes are inserted in the relevant section of the data block. In known digital sound media, the numbering and/or title of the individual recordings, for example, is provided as the additional information.

Figure 17:
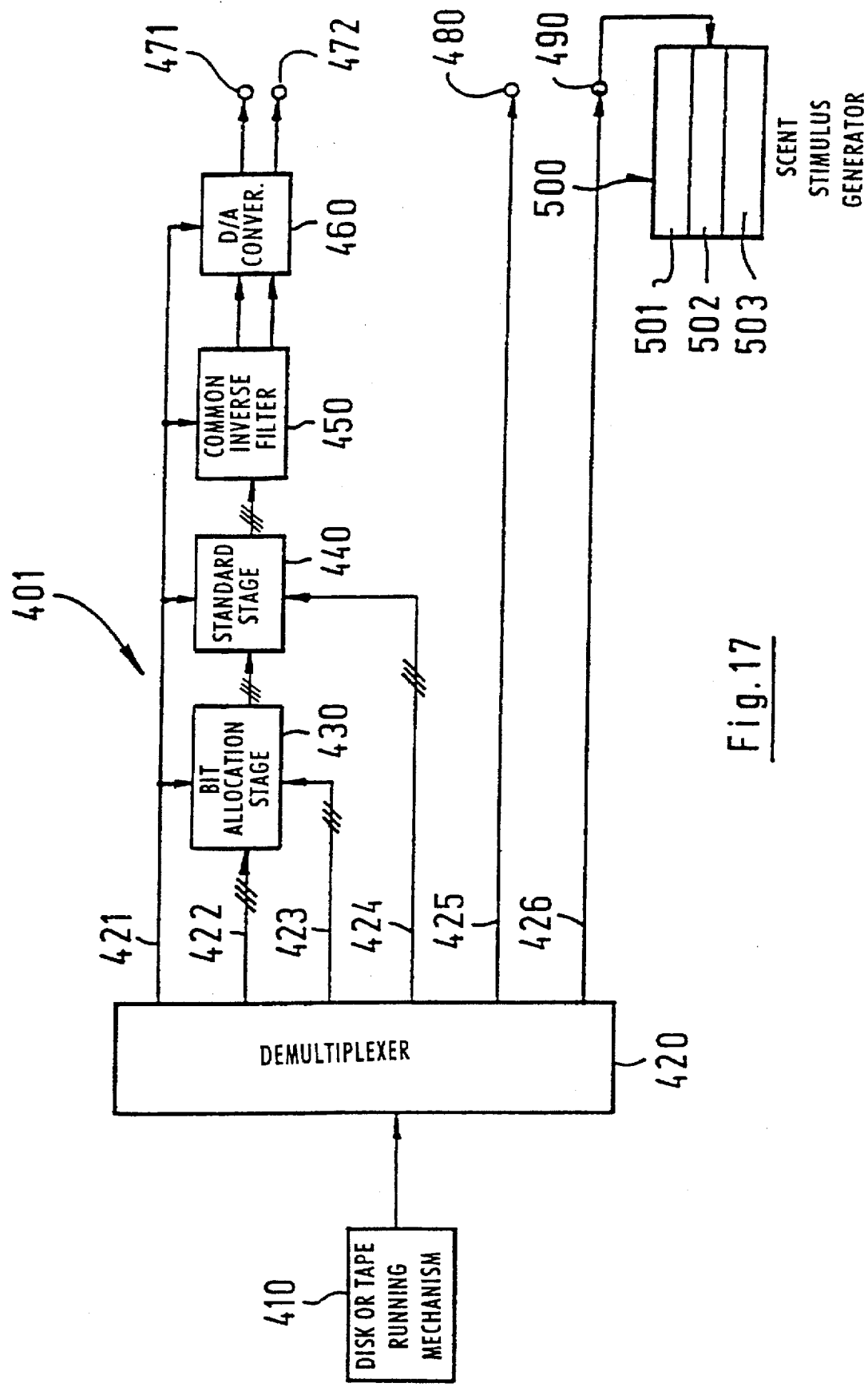
FIG. 17: is a block diagram of a decoder for data blocks shown in FIG. 16.

According to the invention, there is inserted in the section of each data block reserved for additional information, in addition to or instead of the conventional additional information, special control information for a visual, acoustic and/or scent-producing stimulus generator 500 (FIG. 17). That control information differs from the other additional information by correspondingly different coding or by suitable identification bits. The coding of the control information is matched to the coding of the sampling values (subband or transformation coding) thereby enabling in an advantageous manner a multiplex of the data of the digitalized audio signal (including additional information) and of the data of the control information according to the invention.

Figure 16:
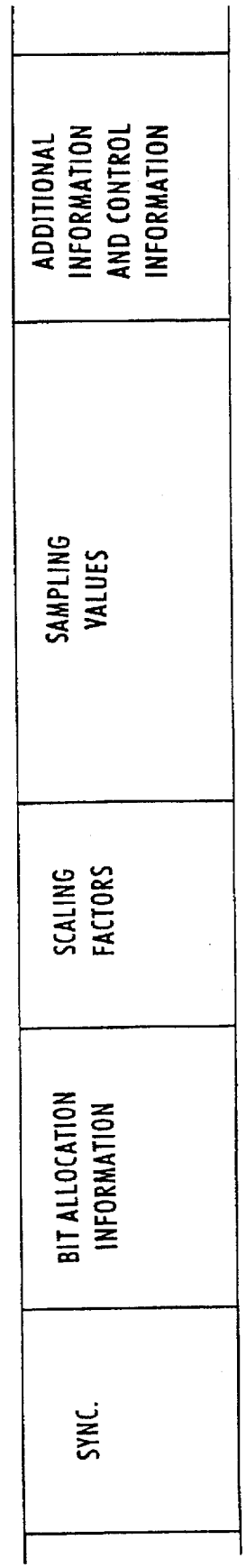
FIG. 16: is a schematic representation of a data block of the data stream shown in FIG. 15.

The decoding of data blocks shown in FIG. 16 in a playback device is explained with reference to the block diagram shown in FIG. 17. The disc or tape running mechanism 410 of the playback device reads the data stream shown in FIG. 15 and transmits it to the demultiplexer 420 of the decoder 401. From the serially incoming data blocks of the data stream the demultiplexer 420 selects the sections contained in each data block and provides the relevant data bits at separate outputs 421 to 426. In the example shown in FIG. 17 the synchronizing information "Sync" is passed to the output 421, the sampling values are passed to the output 422, the bit allocation information is passed to the output 423, the scaling factors are passed to the output 424, the conventional additional information is passed to the output 425, and the control information according to the invention is passed to the output 426.

In the case where the digitalized audio signal is divided into 16 sub-bands (sub-band coding), the outputs 422, 423, 424 and 425 are each in the form of a 16-line bunch with one line per sub-band. A separate series-connection of the blocks 430, 440 and 450 (FIG. 17) is provided for each sub-band, as indicated by three oblique strokes in the supply and connection lines to and between the blocks 430, 440 and 450. The following discussion of the operation of the blocks 430, 440 and 450 applies, therefore, in identical manner to each sub-band.

The sequence of sampling values at the output 422 is passed to a bit allocation stage 430 the control input 431 of which is connected to the output 423. In accordance with the bit allocation information at the control input 431 the irrelevance-reduced sampling values are dequantized and, in the subsequent standardising stage 440, are adjusted in level with the aid of the scaling factors present therein at the control input 441. When standardisation has been completed, all 16 sub-band signals are passed to the common inverse filter 450 and are there combined to form a broad-band, stereophonic digital signal. This stereophonic digital signal is converted in the digital-to-analogue converter 460 into an analogue signal and is available with its left portion L at the output 471 and with its right portion R at the output 472 of the decoder 401.

The additional information present at the output 425 of the demultiplexer 420 is passed to an output 480 of the decoder 401, whereas the control information according to the invention, which is present at the output 426 of the demultiplexer, is provided at an output 490 of the decoder 410. A stimulus generator 500 may be connected to the output 490, which stimulus generator is schematically subdivided into an optical part 501, an acoustic part 502 and a scent-producing part 503. In practice, the parts 501 to 503 of the stimulus generator will be separate devices whose control inputs are each connected to the output 490 of the decoder 401 via a data bus connection. The construction of the parts 501 to 503 of the stimulus generator 500 shown by way of illustration has already been explained above. Instead of microcapsules containing scents that can be released by ultrasound signals it is also possible as an alternative to use scent bottles whose closing member is controlled via a solenoid valve by the digital control information at the output 490 of the decoder 401. For the optical part 501 of the stimulus generator 500 it is possible to use, for example, a so-called "light organ" with variously coloured lamps which can be swivelled, optionally by motors, according to predetermined programs to obtain constantly changing illumination effects in a room. Both the sequence of the colours and the movement of the individual colour lamps can be controlled with the aid of the control information at the output 490 of the decoder 401 in order, for example, to vary the illumination of a room rhythmically in keeping with the music.

In the case of a sound generator as part 502 of the stimulus generator 500, instead of or in addition to the control information at the output 490 there may be used for control purposes also the scaling factors which—as already mentioned—represent the envelope or enveloping curve of the digitalized audio signal. By directly reproducing that envelope or by modulating sound oscillations with that envelope special sound effects are produced which, when reproduced in addition to the audio signal recorded, are able to produce calming or stimulating effects on the listener.

Figure 18:
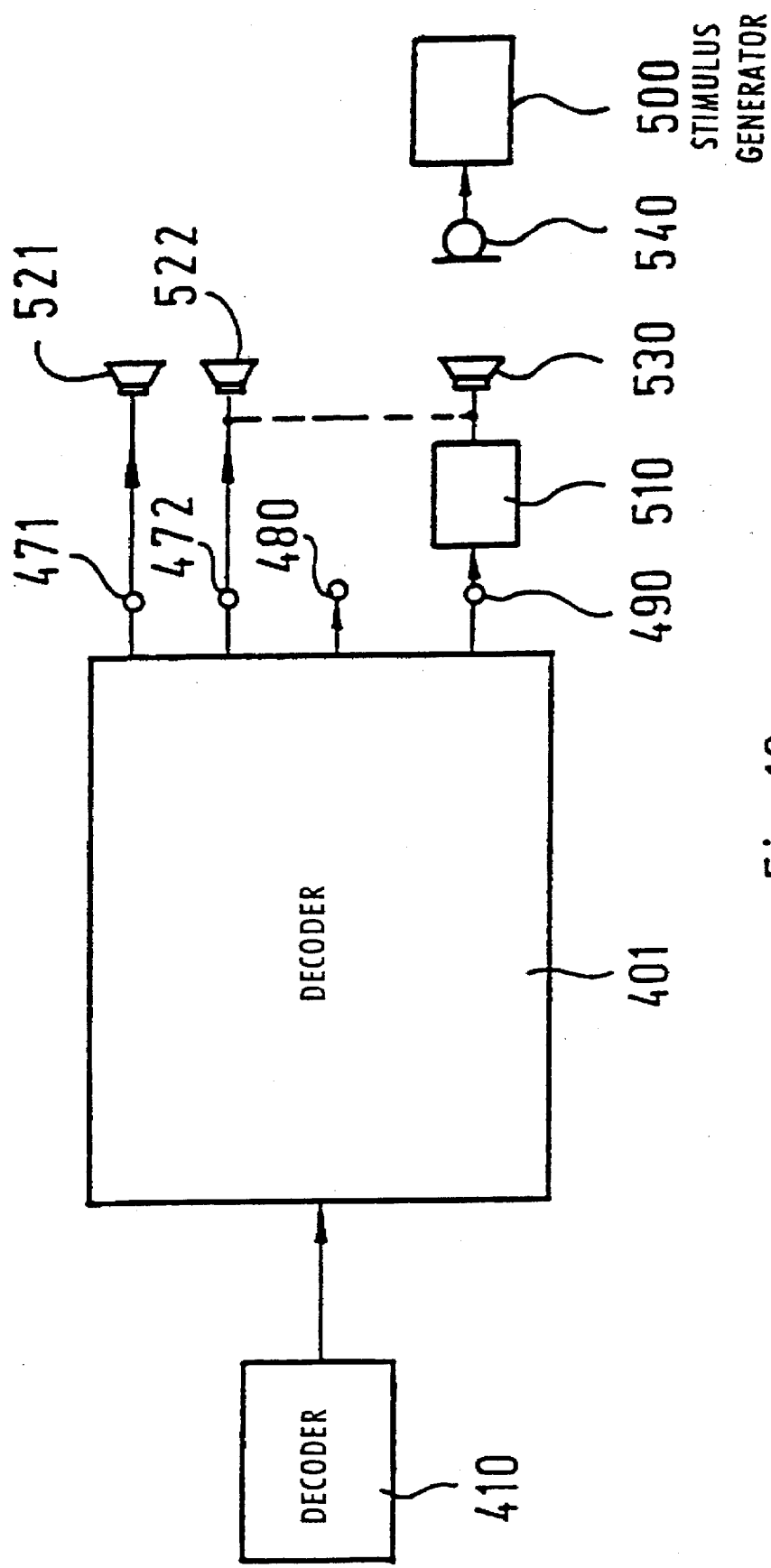
FIG. 18: is a block diagram of an embodiment of a playback device having the decoder shown in FIG. 17.

Instead of an electrical connection between the stimulus generator 500 and the control information at the output 490, an acoustic coupling in the sense of a wireless remote control of the stimulus generator 500 is also possible, as shown with the aid of FIG. 18. For this purpose, the control information at the output 490 is passed to a sound generator 510 which generates a sound signal in the audible or inaudible (ultrasound) region. That sound signal is broadcast either via a separate electro-acoustic transducer 530 or—in the case of an audible sound signal—via one (521) of the loudspeakers 521, 522 of the playback device which are connected via amplifiers (not shown) to the outputs 471 and 472, respectively, for the analogue stereophonic audio signal. The stimulus generator 500 is in this instance provided with a microphone 540 which detects the audible or inaudible sound signal and passes it as control information to the control input of the stimulus generator 500. An audible sound signal can be so selected that—similarly to the above-mentioned use of the envelope of the audio signal—a calming or stimulating effect can be produced on the listener.

Although the present invention has been described and illustrated in detail, it should be clearly understood that the same is by way of illustration and example only and is not to be taken by way of limitation, the spirit and scope of the present invention being limited only by the terms of the appended claims.

I claim:

1. A device for generating sounds and/or pictures, comprising a utility signal source for audio and/or video signals and, connected thereto, an output unit for outputting sounds and/or pictures, comprising a control signal source and at least one stimulus generator controlled by said control signal source, wherein the stimulus generator control signals have a low rate of variation in comparison with the utility signals, wherein the control signal source includes:

a control signal generator and, connected thereto, a control signal memory, and also a control unit by means of which the control signal memory can be activated for the purpose of reading control signals in or out; and wherein the control signal memory is a digital memory and its memory cells are addressed during the read-out operation by an addressing counter whose counting terminal (c) is connected to the output of a slow free-running clock, whereas the addressing of the control signal memory during the reading-in of the control signals is effected by the control unit in dependence upon the incoming control signals.

2. The device according to claim 1 wherein:

the control signal source actuates a plurality of stimulus generators via a control signal decoder.

3. The device according to claim 1, wherein:

the utility signal source has a radio/television broadcast receiving part, and wherein the control signal source comprises a control signal filter which filters control signals, distinguished by one of frequency, time, or separating signals, from the stream of signals emitted by an input circuit of the radio/television broadcast receiving part.

4. The device according to claim 1, wherein:

the utility signal source includes a recording medium for sound and/or pictures in which tracks containing audio and/or video signals are provided on a medium, wherein control signals for actuating the stimulus generator are additionally provided on the medium.

5. The device according to claim 1, wherein:

control signal track groups each associated with one of the audio and/or video signal control groups are recorded contiguously in a control signal track region, with control signal track groups for various pieces of music being separated an preferably also identified by separating signals, and wherein a partial addressing of the control signal memory during reading-out by the control unit is effected according to the number of the particular piece of music to be played.

6. The device according to claim 1, wherein:

the control signal generator comprises a control signal medium and an associated reading device or a control signal entering unit.

7. The device according to claim 1, wherein:

the control signal source has phase-coupling means to which the audio and/or video utility signal is applied.

8. The device according to claim 7, wherein:

the phase-coupling means have a filter circuit to which the audio signal is applied.

9. The device according to claim 7, wherein:

the phase-coupling means has an intermediate output of a frequency divider of a musical instrument, which frequency divider is provided for producing musical accompaniment.

10. The device according to claim 1, wherein:

the control signal source has an adjustable frequency divider or frequency multiplier to which the utility signal is applied.

11. The device according to claim 1, wherein:

the control signal source has an envelope generator.

12. The device according to claim 1, wherein:

at least one of the controllable stimulus generators is a controllable scent generator.

13. The device according to claim 12, wherein:

at least one of the controllable scent generators comprises a controllable carrier gas generator and a selected volume of a scent material through which the carrier gas bubbles.

14. The device according to claim 13, wherein:

the carrier gas is oxygen or oxygen-enriched air.

15. The device according to claim 12, wherein:

at least one of the controllable scent generators comprises a scent carrier consisting of a base and at least one microencapsulated scent applied thereto, and a controllable capsule-breaking device which interacts successively with different regions of the scent carrier.

16. The device according to claim 15, wherein:

the scent carrier is in the form of a web and is drawn off a supply reel by the capsule-breaking device which comprises squeezing rollers.

17. The device according to claim 12, wherein:

the controllable scent generator comprises a pressurizable container filled with a liquid containing at least one scent, at least one spray tube immersed in the liquid, and respective controllable release valve installed in the at least one spray tube.

18. The device according to claim 17, wherein:

a plurality of containers for respective liquids containing corresponding scents are combined to form a container block.

19. The device according to claim 17, wherein:

a fan is arranged in the vicinity of the at least one spray tube.

20. The device according to claim 12, wherein:

at least one of the scent generators comprises a substrate and, arranged thereon, microcapsules containing a scent, wherein a wall material of the microcapsules is either brittle and can be ruptured by sound or is flexible and porous, and a sound generator which directs sound at the microcapsules.

21. The device according to claim 20, wherein:

the microcapsules comprise a mixture of different capsules that respectively respond at different frequencies and/or different sound intensities, selected from a group consisting of capsules with differing wall materials, capsules with differing diameters, and capsules with differing wall thicknesses.

22. The device according to claim 20, wherein:

the sound generator is a loudspeaker of an audio playback device.

23. The device according to claim 20, wherein:

the sound generator is an ultrasound generator which is arranged in the immediate vicinity of the substrate carrying the microcapsules.

24. The device according to claim 22, wherein:

a hard wall is arranged behind the substrate.

25. The device according to claim 1, wherein:

the substrate is in tape form and is moved past the sound generator by a drive in accordance with a scent control signal.

26. The device according to claim 1, wherein:

the stimulus generator control signal simultaneously controls a tone generator the output signal of which is mixed with the audio utility signal.

27. The device according to claim 1, wherein:

at least one of the controllable stimulus generators cooperates with a coupling microphone or a light detector which responds to signals associated with the control signals and operates concurrently via a loudspeaker or a field-scanning generator, respectively.

28. The device according to claim 27, wherein:

a stimulus generator operating unit, in which at least one of the coupling microphone and the stimulus generator is accommodated in a common housing.

29. The device according to claim 1, wherein:

one of the stimulus generators is a color television set to which the control signals are applied via a signal converter.

30. An appliance for generating sounds and/or images, comprising:

a light generator and a light control unit associated therewith to provide a light control signal, said light control unit comprising a light signal envelope generator;

a sound generator and a sound control unit associated therewith to provide a sound control signal;

means for providing a phase coupling of the light control signal and the sound control signal generating an output signal to activate at least one controllable source of fragrance.

* * * * *